United States Patent
Liversidge et al.

(12)

(10) Patent No.: US 6,270,806 B1
(45) Date of Patent: Aug. 7, 2001

(54) USE OF PEG-DERIVATIZED LIPIDS AS SURFACE STABILIZERS FOR NANOPARTICULATE COMPOSITIONS

(75) Inventors: Elaine Liversidge, West Chester; Greta A. Gottardy, Lansdale, both of PA (US)

(73) Assignee: Elan Pharma International Limited, Shannon (IE)

(*) Notice: Subject to any disclaimer, the term of this patent is extended or adjusted under 35 U.S.C. 154(b) by 0 days.

(21) Appl. No.: 09/261,151

(22) Filed: Mar. 3, 1999

(51) Int. Cl.[7] ....................................... A61K 9/16
(52) U.S. Cl. .................... 424/497; 424/502; 514/169; 514/458; 514/725
(58) Field of Search .................... 424/422, 489–492, 424/502; 514/169, 458, 725

(56) References Cited

U.S. PATENT DOCUMENTS

| | | |
|---|---|---|
| 5,145,684 | 9/1992 | Liversidge et al. . |
| 5,336,507 | 8/1994 | Na et al. . |
| 5,470,583 | 11/1995 | Na et al. . |
| 5,643,552 | * 7/1997 | Illig ........................................ 424/9.45 |
| 5,668,196 | 9/1997 | Robinson et al. . |
| 5,670,136 | 9/1997 | Bacon et al. . |
| 5,672,662 | 9/1997 | Harris et al. . |
| 5,718,919 | 2/1998 | Ruddy et al. . |
| 5,747,001 | 5/1998 | Wiedmann et al. . |
| 5,834,025 | 11/1998 | de Garavilla et al. . |
| 5,922,357 | * 7/1999 | Coombes .............................. 424/491 |

FOREIGN PATENT DOCUMENTS

| | | |
|---|---|---|
| 275796 | 3/1992 | (EP) . |
| 499 299 A2 | 8/1992 | (EP) . |
| WO 90/07923 | 7/1990 | (WO) . |

OTHER PUBLICATIONS

Stedman's Medical Dictionary, 25th Edition, pp. 884 (Williams & Wilkins, Baltimore, MD, 1990).
Hawley's Condensed Chemical Dictionary, 11th Edition, pp. 704 (Van Nostrand Reinhold Co., New York, 1987).

(List continued on next page.)

Primary Examiner—Gollamudi S. Kishore
(74) Attorney, Agent, or Firm—Foley & Lardner

(57) ABSTRACT

Nanoparticulate compositions comprising an insoluble organic drug and at least one polyethylene glycol-derivatized lipid adsorbed on the surface of the drug are described. The polyethylene glycol-derivatized lipid can be a PEG-phospholipid, PEG-cholesterol, PEG-cholesterol derivative, PEG-vitamin A, PEG-vitamin E, or a mixture thereof The compositions have an effective average particle size of less than about 1 micron. The invention also describes methods of making and using such compositions.

49 Claims, 11 Drawing Sheets

U.S. PATENT DOCUMENTS

Kimelberg et al., "Properties and Biological Effects of Liposomes and Their Uses in Pharmacology and Toxicology," *CRC Crit. Rev. Toxicol.*, 6:25–79 (1978).

Allen et al., "Stealth® Liposomes: An Improved Sustained Release System For 1–beta–D–arabinofuranosyl–cytosine," *Cancer Res.*, 521:2431–2439 (1992).

Yuda et al., "Prolongation of Liposome Circulation Time by Various Derivatives of Polyethyleneglycols," *Biol. Pharm. Bull.*, 19:1347–1351, 1347–1348 (1996).

Allen, "Long–circulating (sterically stabilized) liposomes for targeted drug delivery," *TiPS*, 15:215–220 (1994).

Lasic D., "Liposomes," *Am. Scientist*, 80:20–31 (1992).

Papahadjopoulos et al., "Sterically Stabilized Liposomes; Pronounced Improvements in Blood Clearance, Tissue Distribution, and Therapeutic Index of Encapsulated Drugs Against Implanted Tumors," *PNAS*, USA, 88:11460–11464 (1991).

Bedu–Addo et al., "Interaction of PEG–phospholipid Conjugates with Phospholipid Implications in Liposomal Drug Delivery," *Advanced Drug Delivery Reviews*, 16:235–247 (1995).

Lasic et al., "The 'Stealth' Liposome: A Prototypical Biomaterial," *Chemical Reviews*, 95:2601–2628 (1995).

Mayhew et al., *Int. J. Cancer*, 51:302–309 (1992).

Huang et al., *Cancer Res.*, 52:6774–6781 (1992).

Gabizon et al., "A Pilot Study of Doxorubicin Encapsulated in Long–Circulating (Stealth®) Liposomes (S–Dox) In Cancer Patients," *Proc. Am. Soc. Clin. Oncol.* 11:124 (1992).

Non–stealth (poly(lactic acid/albumin)) and stealth (poly-(lactic acid–polyethylene glycol)) nanoparticles as injectable drug carriers, T. Verrecchia et al., Journal of Controlled Release 36 (1995) 49–61.

Ismailos et al., "Enhancement of cyclosporin A solubility by d–alphatocopheryl–polyethylene–glycol–100 succinate (TPGS)," *European Journal of Pharmaceutical Science*, 269–271 (1994).

\* cited by examiner

2% Compound A + 0.5% Albumin

2% Compound A + 1% Cremophor EL

2% Compound A + 1% F108

2% Compound A + 1% F108 in dextrose

2% Compound A + 1% F108 + 0.005% DOSS

2% Compound A + 1% F108 in saline

2% Compound A + 1% HPC-SL

2% Compound A + 1% Tyloxapol

2% Compound A + 1% Vitamin E PEG

2% Compound A + 1% PEG-5000 Phospholipid in saline

2% Compound A + 1% PVP C-15

2% Compound A + 2% Tween 80

2% Compound A + 1% PEG-5000 Phospholipid

2% Compound B and 2% tyloxapol

USE OF PEG-DERIVATIZED LIPIDS AS SURFACE STABILIZERS FOR NANOPARTICULATE COMPOSITIONS

FIELD OF THE INVENTION

The present invention is directed to nanoparticulate formulations of a drug having at least one polyethylene glycol (PEG)-derivatized phospholipid, PEG-derivatized cholesterol, PEG-derivatized cholesterol derivative, PEG-derivatized vitamin A, or PEG-derivatized vitamin E adsorbed on the surface of the drug as a surface stabilizer, and methods of making and using such compositions.

BACKGROUND OF THE INVENTION

Nanoparticulate compositions, first described in U.S. Pat. No. 5,145,684 ("the '684 patent"), are particles consisting of a poorly soluble therapeutic or diagnostic agent having adsorbed onto the surface thereof a non-crosslinked surface stabilizer. The '684 patent describes the use of a variety of surface stabilizers for nanoparticulate compositions. The use of a PEG-derivatized phospholipid, PEG-derivatized cholesterol, PEG-derivatized cholesterol derivative, PEG-derivatized vitamin A, or PEG-derivatized vitamin E as a surface stabilizer for nanoparticulate compositions, or any other component of such compositions, is not described by the '684 patent.

The '684 patent describes a method of screening drugs to identify useful surface stabilizers that enable the production of a nanoparticulate composition. Not all surface stabilizers will function to produce a stable, non-agglomerated nanoparticulate composition for all drugs. Moreover, known surface stabilizers may be unable to produce a stable, non-agglomerated nanoparticulate composition for certain drugs. Thus, there is a need in the art to identify new surface stabilizers useful in making nanoparticulate compositions. Additionally, such new surface stabilizers may have superior properties over prior known surface stabilizers.

A. Lipids in Nanoparticulate Compositions

A lipid is an inclusive term for fats and fat-derived materials. It includes all substances which are (i) relatively insoluble in water but soluble in organic solvents (benzene, chloroform, acetone, ether, etc.); (ii) related either actually or potentially to fatty acid esters, fatty alcohols, sterols, waxes, etc.; and (iii) utilizable by the animal organism. Because lipids are relatively insoluble in water, but soluble in organic solvents, lipids are often referred to as "fat soluble," denoting substances extracted from animal or vegetable cells by nonpolar or "fat" solvents. Exemplary lipids include phospholipids (such as phosphatidylcholine, phosphatidylethanolamine, and cephalin), fats, fatty acids, glycerides and glycerol ethers, sphingolipids, alcohols and waxes, terpenes, steroids, and "fat soluble" vitamins A or E, which are non-cholesterol based poorly water soluble vitamins. *Stedman's Medical Dictionary*, 25th Edition, pp. 884 (Williams & Wilkins, Baltimore, Md., 1990); *Hawley's Condensed Chemical Dictionary*, 11th Edition, pp. 704 (Van Nostrand Reinhold Co., New York, 1987).

A number of U.S. patents teach the use of a charged phospholipid, such as dimyristoyl phophatidyl glycerol, as an auxiliary surface stabilizer for nanoparticulate compositions. See e.g., U.S. Pat. No. 5,834,025 for "Reduction of Intravenously Administered Nanoparticulate-Formulation-Induced Adverse Physiological Reactions"; U.S. Pat. No. 5,747,001 for "Aerosols Containing Beclomethasone Nanoparticle Dispersions"; and U.S. Pat. No. 5,718,919 for "Nanoparticles Containing the R(−)Enantiomer of Ibuprofen."

Other U.S. patents describe the use of a charged phospholipid, such as diacylphosphatidyl glycerol or dimyristoyl phosphatidyl glycerol, as a cloud point modifier for the surface stabilizer of a nanoparticulate composition to prevent particle aggregation during steam heat autoclaving. See e.g., U.S. Pat. No. 5,670,136 for "2,4,6-triiodo-5-substituted-amino-isophthalate Esters Useful as X-ray Contrast Agents for Medical Diagnostics Imaging"; U.S. Pat. No. 5,668,196 for 3-amido-triiodophenyl Esters as X-ray Contrast Agents"; U.S. Pat. No. 5,643,552 for "Nanoparticulate Diagnostic Mixed Carbonic Anhydrides as X-ray Contrast Agents for Blood Pool and Lymphatic System Imaging"; U.S. Pat. No. 5,470,583 for "Method of Preparing Nanoparticle Compositions Containing Charged Phospholipids to Reduce Aggregation"; and U.S. Pat. No. 5,336,507 for "Use of Charged Phospholipids to Reduce Nanoparticle Aggregation." None of these patents refer to the use of a PEG-derivatized phospholipid, PEG-derivatized cholesterol, PEG-derivatized cholesterol derivative, PEG-derivatized vitamin A, or PEG-derivatized vitamin E in nanoparticulate compositions, either as a surface stabilizer, cloud point modifier, or as any other constituent of a nanoparticulate composition.

B. PEG-derivatized Lipids in Pharmaceutical Compositions

Liposomes, or vesicles composed of single or multiple phospholipid bilayers, have been investigated as possible carriers for drugs. Unmodified liposomes tend to be taken up in the liver and spleen. For drugs targeted to these areas, unmodified liposomes are useful drug adjuvants. However, often the liver and spleen are not the target areas for drug delivery. This affinity for the liver and spleen limits the effectiveness of liposome-encapsulated drugs and complicates dosing. Kimelberg et al., "Properties and Biological Effects of Liposomes and Their Uses in Pharmacology and Toxicology," *CRC Crit. Rev. Toxicol.*, 6:25–79 (1978); and Allen et al., "Stealth® Liposomes: An Improved Sustained Release System For 1-beta-D-arabinofuranosyl-cytosine," *Cancer Res.*, 521:2431–2439 (1992). To avoid these problems, researchers have studied various ways of modifying the liposome structure to prolong circulation time. Allen, *Cancer Res.*, 521:2431–2439 (1992).

It was discovered that one useful type of modified lipid contains polyethylene glycol (PEG). In its most common form PEG, also known as poly(ethylene oxide) (PEO), is a linear polymer terminated at each end with hydroxyl groups:

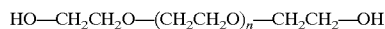

This polymer can be represented as HO-PEG-OH, where it is understood that the –PEG-symbol represents the following structural unit:

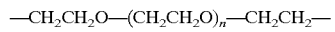

PEG is particularly useful because of its ease of preparation, relatively low cost, controllability of the molecular weight, and the ability to link to lipid by various methods. PEG is believed to act by forming a hydrophilic coat and by causing steric hindrance at the liposome surface, thus reducing liposome-serum protein interaction and liposome-RES (reticuloendothelial system) cells interaction. Yuda et al., "Prolongation of Liposome Circulation Time by Various Derivatives of Polyethyleneglycols," *Biol. Pharm. Bull.*, 19:1347–1351, 1347–1348 (1996).

PEG-derivatized lipids are described in, for example, U.S. Pat. No. 5,672,662 ("the '662 Patent") for "Poly(Ethylene Glycol) and Related Polymers Monosubstituted with Propionic or Butanoic Acids and Functional Derivatives Thereof for Biotechnical Applications," and Yuda et al. (1996).

1. PEG-Derivatized Lipid Drug Carriers Result in Increased In Vivo Circulation Times of the Administered Drug PEG derivatized lipids or liposomes are referred to as "sterically stabilized" lipids or liposomes (S-lipids or S-liposomes). Allen, "Long-circulating (sterically stabilized) liposomes for targeted drug delivery," *TiPS*, 15:215–220 (1994). PEG attracts water to the lipid surface, thus forming a hydrophilic surface on the lipid. The hydrophilic surface inhibits opsonization of the lipid by plasma proteins, leading to increased survival times of PEG-lipid in the circulation. Opsonization refers to uptake by the cells of the mononuclear phagocyte system (MPS), located primarily in the liver and spleen. Because PEG-derivatized lipids evade the cells of the MPS, they are often called Stealth® lipid or liposomes. Lasic D., "Liposomes," *Am. Scientist*, 80:20–31 (1992); Papahadjopoulos et al., "Sterically Stabilized Liposomes; Pronounced Improvements in Blood Clearance, Tissue Distribution, and Therapeutic Index of Encapsulated Drugs Against Implanted Tumors," *PNAS, U.S.A.*, 88:11460–11464 (1991). (Stealth® is a registered trade mark of Liposome Technology, Inc., Menlo Park, Calif.)

The diagram below shows a representative PEG-liposome as compared to a conventional liposome:

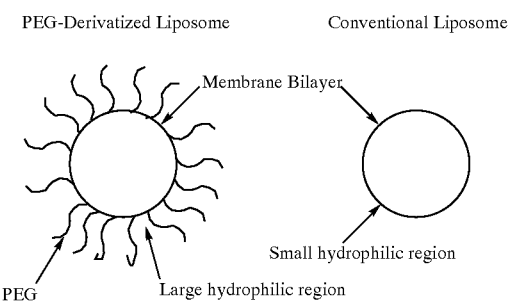

PEG-lipids are highly superior over conventional lipids as they exhibit: (1) prolonged blood residence times, (2) a decreased rate and extent of uptake into the MPS with reduced chance of adverse effects to this important host defense system, (3) dose-independent pharmakokinetics in animals and humans, and (4) the ability to cross in vivo biological barriers. Allen at 216; Yuda et al. at 1349–1351; Bedu-Addo et al., "Interaction of PEG-phospholipid Conjugates with Phospholipid Implications in Liposomal Drug Delivery," *Advanced Drug Delivery Reviews*, 16:235–247 (1995); and Lasic et al., "The 'Stealth' Liposome: A Prototypical Biomaterial," *Chemical Reviews*, 95:2601–2628 (1995).

For example, it has been reported that PEG-derivatized lipids can result in a great increase in the blood circulation lifetime of the particles. Studies of doxorubicin and epirubicin encapsulated in PEG-phospholipids for decreasing tumor size and growth showed that the encapsulated drugs had a much longer half-life than free drug and are cleared much more slowly from the circulation (for PEG-phospholipid encapsulated doxorubicin, the distribution half-life was about 42 hours, in contrast to the distribution half-life of about 5 minutes for free doxorubicin). The '662 Patent; Mayhew et al., *Int. J. Cancer*, 51:302–309 (1992); Huang et al., *Cancer Res.*, 526774–6781 (1992); and Gabizon et al., "A Pilot Study of Doxorubicin Encapsulated in Long-Circulating (Stealth®) Liposomes (S-Dox) In Cancer Patients," *Proc. Am. Soc. Clin. Oncol.* 11:124 (1992).

Similarly, Yuda et al. describe prolongation of the in vivo circulation time of PEG-derivatized lipids, such as PEG-derivatized cholesterol, PEG-derivatized succinate, PEG-derivatized phosphatides, and PEG-derivatized glycerols. The results showed that incorporation of the PEG-derivatives into liposomes appreciably increased the blood level of liposomes and correspondingly decreased the RES uptake after injection. Conventional liposomes without PEG showed low blood levels and high accumulation in the liver and spleen, suggesting that these liposomes were readily taken up by the RES. Yuda et al. at 1349.

2. PEG-Derivatized Lipid Drug Carriers Result in Decreased Toxicity of the Administered Drug In addition to the prolonged half-life of drugs when encapsulated in PEG-derivatized lipids, it was also determined that toxicity of the administered drug is reduced compared to that observed with administration of free drug in animals. This reduction in toxicity is likely because the PEG-liposome carrier prevents a large post-administration spike in plasma levels. Mayhew et al., *Int. J. Cancer*, 51:302–309 (1992).

3. PEG-Derivatized Lipid Drug Carriers Result in Increased Stability of the Administered Drug Another way in which long-circulating PEG-lipids may enhance cytotoxic cell delivery is by protecting drugs that rapidly degrade from contact with plasma for prolonged periods. For example, in a study of mice bearing leukemia tumors, ARA-C (an unstable drug) encapsulated in PEG-derivatized phospholipids was more effective at lower doses in prolonging survival time of mice than was free ARA-C or ARA-C entrapped in conventional liposomes. Allen et al., *Cancer Res.*, 521:2431–2439 (1992). The superiority of the PEG-derivatized phospholipid delivery system to other drug delivery systems at low doses was attributed to the greatly extended circulation time of the PEG-derivatized lipids, as well as to slow leakage rates of the drug from the carrier.

There is a need in the art for nanoparticulate compositions of poorly soluble drugs having potentially long blood pool residence times, decreased toxicity, and increased stability to increase the effectiveness of the administered drug, and for methods of making such compositions. In addition, there is a need in the art for a surface stabilizer useful in preparing nanoparticulate compositions of drugs, in which prior known surface stabilizers are ineffective. The present invention satisfies these needs.

SUMMARY OF THE INVENTION

The present invention is directed to nanoparticulate compositions comprising a poorly soluble drug and at least one PEG-derivatized phospholipid ("PEG-phospholipid"), PEG-derivatized cholesterol ("PEG-cholesterol"), PEG-derivatized cholesterol derivative ("PEG-cholesterol derivative"), PEG-derivatized vitamin A ("PEG-vitamin A"), or PEG-derivatized vitamin E ("PEG-vitamin E") surface stabilizer adsorbed to the surface of the drug. Because of the stability of PEG-lipids, drug/PEG-lipid nanoparticulate compositions afford enhanced blood pool residence times, decreased toxicity, and increased stability of an administered drug Another aspect of the invention is directed to pharmaceutical compositions comprising a nanoparticulate composition of the invention. The pharmaceutical composition preferably comprises a poorly soluble drug, at least one PEG-phospholipid, PEG-cholesterol, PEG-cholesterol derivative, PEG-vitamin A, or PEG-vitamin E surface stabilizer adsorbed to the surface of the drug, and a pharmaceutically acceptable carrier, as well as any desired excipients.

This invention further discloses a method of making a nanoparticulate composition having at least one PEG-phospholipid, PEG-cholesterol, PEG-cholesterol derivative, PEG-vitamin A, or PEG-vitamin E surface stabilizer adsorbed on the surface of the drug. Such a method comprises contacting a poorly soluble nanoparticulate drug with at least one PEG-phospholipid, PEG-cholesterol, PEG-cholesterol derivative, PEG-vitamin A, or PEG-vitamin E surface stabilizer for a time and under conditions sufficient to provide a nanoparticle/PEG-lipid composition. The PEG-lipid surface stabilizers can be contacted with the drug either before, during, or after size reduction of the drug.

The present invention is further directed to a method of treatment comprising administering to a mammal in need a therapeutically effective amount of a nanoparticulate drug/PEG-lipid composition according to the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

Figure 1A:
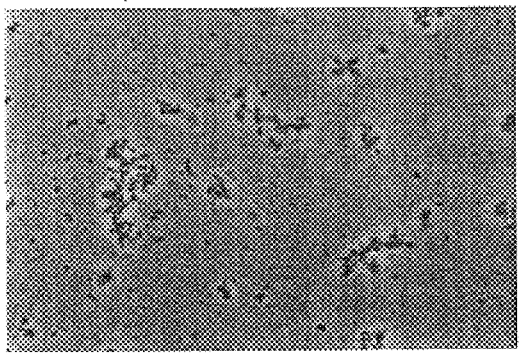
FIG. 1a: Shows a photomicrograph of a composition of 2% Compound A and 0.5% albumin following milling.

The present invention is directed to a composition comprising nanoparticulate drug having at least one PEG-phospholipid, PEG-cholesterol, PEG-cholesterol derivative, PEG-vitamin A, or PEG-vitamin E surface stabilizer adsorbed on the surface thereof, and methods of making and using such nanoparticulate compositions.

A. Compositions

The compositions of the invention comprise nanoparticulate drug and at least one PEG-phospholipid, PEG-cholesterol, PEG-cholesterol derivative, PEG-vitamin A, or PEG-vitamin E surface stabilizer adsorbed to the surface of the drug. Surface stabilizers useful herein physically adhere to the surface of the nanoparticulate drug, but do not chemically react with the drug or itself. Individually adsorbed molecules of the surface stabilizer are essentially free of intermolecular cross-linkages.

The present invention also includes nanoparticulate compositions having at least one PEG-phospholipid, PEG-cholesterol, PEG-cholesterol derivative, PEG-vitamin A, or PEG-vitamin E surface stabilizer adsorbed on the surface thereof, formulated into compositions together with one or more non-toxic physiologically acceptable carriers, adjuvants, or vehicles, collectively referred to as carriers. The compositions can be formulated for parenteral injection, oral administration in solid or liquid form, rectal or topical administration, and the like.

1. Drug Particles

The nanoparticles of the invention comprise a therapeutic or diagnostic agent, collectively referred to as a "drug." A therapeutic agent can be a pharmaceutical agent, including biologics such as proteins, peptides, and nucleotides, or a diagnostic agent, such as a contrast agent, including x-ray contrast agents. The drug exists either as a discrete, crystalline phase, or as an amorphous phase. The crystalline phase differs from a non-crystalline or amorphous phase which results from precipitation techniques, such as those described in EP Patent No. 275,796.

The invention can be practiced with a wide variety of drugs. The drug is preferably present in an essentially pure form, is poorly soluble, and is dispersible in at least one liquid medium. By "poorly soluble" it is meant that the drug has a solubility in the liquid dispersion medium of less than about 10 mg/mL, and preferably of less than about 1 mg/mL.

The drug can be selected from a variety of known classes of drugs, including, for example, proteins, peptides, nucleotides, anti-obesity drugs, nutriceuticals, corticosteroids, elastase inhibitors, analgesics, anti-fungals, oncology therapies, antiemetics, analgesics, cardiovascular agents, anti-inflammatory agents, anthelmintics, antiarrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radiopharmaceuticals, sex hormones (including steroids), antiallergic agents, stimulants and anoretics, sympathomimetics, thyroid agents, vasodilators and xanthines.

A description of these classes of drugs and a listing of species within each class can be found in Martindale, *The Extra Pharmacopoeia,* Twenty-ninth Edition (The Pharmaceutical Press, London, 1989), specifically incorporated by reference. The drugs are commercially available and/or can be prepared by techniques known in the art.

2. PEG-lipid Surface Stabilizers

Suitable PEG-lipid surface stabilizers can preferably be selected from any PEG-phospholipid, PEG-cholesterol, PEG-cholesterol derivative, PEG-vitamin A, or PEG-vitamin E.

The molecular weight of the PEG substituent on the lipid affects the circulation half life of the compound. Derivatized lipids having a PEG of high molecular mass, such as about 4000 to about 5000 Da, have long circulation half lives, with lower molecular weights of 2000 Da also being useful. Derivatized lipids having lower PEG molecular masses, such as about 750 to about 800 Da are also useful, although the circulation half-life begins to be compromised at this lower molecular weight. Allen at 218; and Yuda et al. at 1349.

Liposomes containing PEG-derivatives and having functional groups at their terminals, such as DPP-PEG-OH and DSPE-PEG-COOH (e.g., α-(dipalmitoylphosphatidyl)-ω-hydroxypolyoxyethylene and distearoylphosphatidyl-N-(3-carboxypropionylpolyoxyethylene succinyl)ethanolamine), also lengthen the circulation half-life of the compounds as compared to non-PEG derivatized compounds and PEG-derivatized compounds of the same molecular weight lacking the functional end group. Yuda et al. at 1349. Moreover, PEG-derivatized compounds having terminal end functional groups and lower molecular weights, e.g., about 1000 Da or less, result in longer circulation times as compared to non-PEG derivatized compounds and PEG-derivatized compounds of the same molecular weight lacking the functional end group Two exemplary commercially available PEG-liposomes are PEG-5000™ and PEG-2000™ (Shearwater Polymers, Inc.).

Two or more surface stabilizers can be used in combination.

3. Auxiliary Surface Stabilizers

The compositions of the invention can also include one or more auxiliary surface stabilizers in addition to the at least one PEG-lipid surface stabilizer. Suitable auxiliary surface stabilizers can preferably be selected from known organic and inorganic pharmaceutical excipients. Such excipients include various polymers, low molecular weight oligomers, natural products, and surfactants. Preferred surface stabilizers include nonionic and ionic surfactants. Two or more surface auxiliary stabilizers can be used in combination.

Representative examples of auxiliary surface stabilizers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxs 3350® and 1450®, and Carbopol 934® (Union Carbide)), dodecyl trimethyl ammonium bromide, polyoxyethylene stearates, colloidal silicon dioxide, phosphates, sodium dodecylsulfate, carboxymethylcellulose calcium, hydroxypropyl celluloses (e.g., HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, dioctylsulfosuccinate (DOSS); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like.

Most of these surface stabilizers are known pharmaceutical excipients and are described in detail in the *Handbook of Pharmaceutical Excipients,* published jointly by the American Pharmaceutical Association and The Pharmaceutical Society of Great Britain (The Pharmaceutical Press, 1986), specifically incorporated by reference. The surface stabilizers are commercially available and/or can be prepared by techniques known in the art.

3. Nanoparticulate Drug/PEG-Lipid Particle Size

Preferably, the compositions of the invention contain nanoparticles which have an effective average particle size of less than about 1000 nm (i.e., 1 micron), more preferably less than about 600 nm, less than about 400 nm, less than about 300 nm, less than about 250 nm, less than about 100 nm, or less than about 50 nm, as measured by light-scattering methods, microscopy, or other appropriate methods. By "an effective average particle size of less than about 1000 nm" it is meant that at least 50% of the drug particles have a weight average particle size of less than about 1000 nm when measured by light scattering techniques. Preferably, at least 70% of the drug particles have an average particle size of less than about 1000 nm, more preferably at least 90% of the drug particles have an average particle size of less than about 1000 nm, and even more preferably at least about 95% of the particles have a weight average particle size of less than about 1000 nm.

4. Concentration of Nanoparticulate Drug and Stabilizer

The relative amount of drug and one or more surface stabilizers can vary widely. The optimal amount of the surface stabilizers can depend, for example, upon the particular active agent selected, the hydrophilic lipophilic balance (HLB), melting point, and water solubility of the PEG-lipid surface stabilizer, and the surface tension of water solutions of the stabilizer, etc.

The concentration of the one or more surface stabilizers can vary from about 0.1 to about 90%, and preferably is from about 1 to about 75%, more preferably from about 10 to about 60%, and most preferably from about 10 to about 30% by weight based on the total combined weight of the drug substance and surface stabilizer.

The concentration of the drug can vary from about 99.9% to about 10%, and preferably is from about 99% to about 25%, more preferably from about 90% to about 40%, and most preferably from about 90% to about 70% by weight based on the total combined weight of the drug substance and surface stabilizer.

B. Methods of Making Nanoparticulate Formulations

The nanoparticulate drug compositions can be made using, for example, milling or precipitation techniques. Exemplary methods of making nanoparticulate compositions are described in the '684 patent.

1. Milling to obtain Nanoparticulate Drug Dispersions

Milling of aqueous drug to obtain a nanoparticulate dispersion comprises dispersing drug particles in a liquid dispersion medium, followed by applying mechanical means in the presence of grinding media to reduce the particle size of the drug to the desired effective average particle size. The particles can be reduced in size in the presence of at least one PEG-phospholipid, PEG-cholesterol, PEG-cholesterol derivative, PEG-vitamin A, or PEG-vitamin E surface stabilizer. Alternatively, the particles can be contacted with one or more surface stabilizers after attrition. Other compounds, such as a diluent, can be added to the drug/surface stabilizer composition during the size reduction process. Dispersions can be manufactured continuously or in a batch mode. The resultant nanoparticulate drug dispersion can be utilized in solid or liquid dosage formulations.

2. Precipitation to Obtain Nanoparticulate Drug Compositions

Another method of forming the desired nanoparticulate composition is by microprecipitation. This is a method of preparing stable dispersions of drugs in the presence of one or more surface stabilizers and one or more colloid stability enhancing surface active agents free of any trace toxic solvents or solubilized heavy metal impurities. Such a method comprises, for example: (1) dissolving the drug in a suitable solvent; (2) adding the formulation from step (1) to a solution comprising at least one surface stabilizer to form a clear solution; and (3) precipitating the formulation from step (2) using an appropriate non-solvent. The method can be followed by removal of any formed salt, if present, by dialysis or diafiltration and concentration of the dispersion by conventional means. The resultant nanoparticulate drug dispersion can be utilized in solid or liquid dosage formulations.

C. Methods of Using Nanoparticulate Drug Formulations Comprising One or More Surface Stabilizers The nanoparticulate compositions of the present invention can be administered to humans and animals either orally, rectally, parenterally (intravenous, intramuscular, or subcutaneous), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include capsules, tablets, pills, powders, and granules. In such solid dosage forms, the active compound is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active ingredients in the nanoparticulate compositions of the invention may be varied to obtain an amount of active ingredient that is effective to obtain a desired therapeutic response for a particular composition and method of administration. The selected dosage level therefore depends upon the desired therapeutic effect, the route of administration, the potency of the administered drug, the desired duration of treatment, and other factors.

The total daily dose of the compounds of this invention administered to a host in single or divided dose may be in amounts of, for example, from about 1 nanomol to about 5 micromoles per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

The purpose of this example was to test the effectiveness of different conventional intravenous surface stabilizers in producing a stable non-agglomerated nanoparticulate composition of Compound A, a poorly water-soluble compound having therapeutic activity.

All of the following formulations (except for the formulation of Pluronic F108™ and 0.005% DOSS) were prepared for roller milling in a 15 ml amber colored bottle filled with 7.5 ml of 0.8 mm YTZ Zirconia media on a U.S. Stoneware mill.

The Pluronic F108™, HPC-SL, tyloxapol, and PVP formulations were milled for 7 days; the albumin, PEG-vitamin E, Pluronic F108™ in saline, PEG-5000 phospholipid in saline, and Chremophor EL™ formulations were milled for 5 days; the Tween 80™ formulation was milled for 4 days; and the Pluronic F108™ in dextrose formulation was milled for 8 days. The formulation of Pluronic F108™ and 0.005% DOSS was DC milled rather than roller milled (DC milling is higher energy than roller milling) in a 15 ml polycarbonate tube with 4 ml of 0.5 mm SDy-20 polymeric media for 22 hours.

The figures referenced for each composition show a photomicrograph of the composition following milling.

Figure 1B:
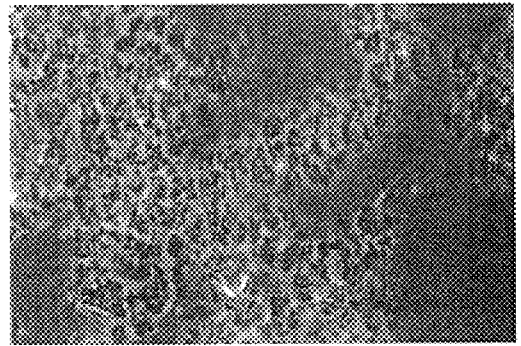
FIG. 1b: Shows a photomicrograph of a composition of 2% Compound A and 1.0% Chremophor EL following milling.
Figure 1C:
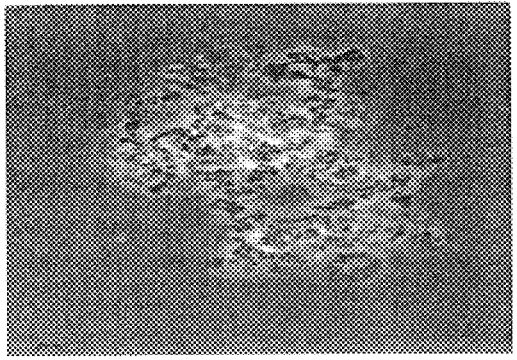
FIG. 1c: Shows a photomicrograph of a composition of 2% Compound A and 1.0% F108 following milling.
Figure 1D:
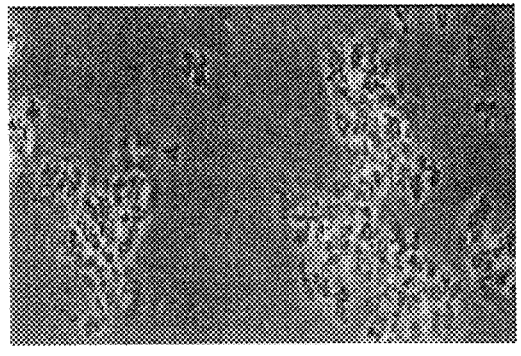
FIG 1d: Shows a photomicrograph of a composition of 2% Compound A and 1.0% F108 in dextrose following milling.
Figure 2A:
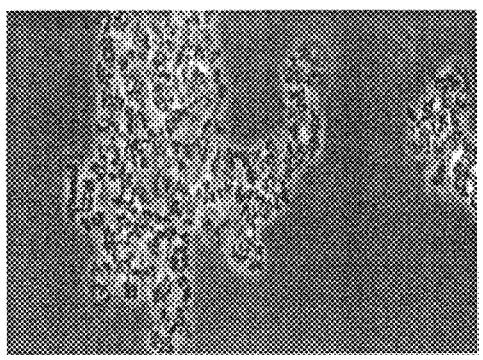
FIG. 2a: Shows a photomicrograph of a composition of 2% Compound A, 1.0% F108, and 0.005% DOSS following milling.
Figure 2B:
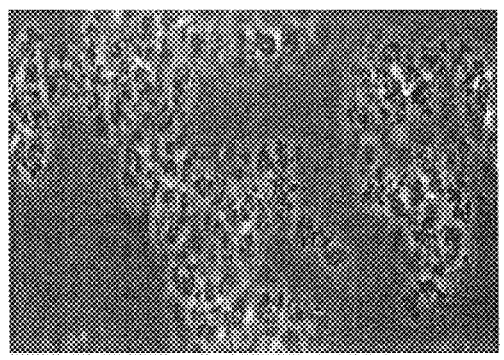
FIG. 2b: Shows a photomicrograph of a composition of 2% Compound A and 1.0% F108 in saline following milling.
Figure 2C:
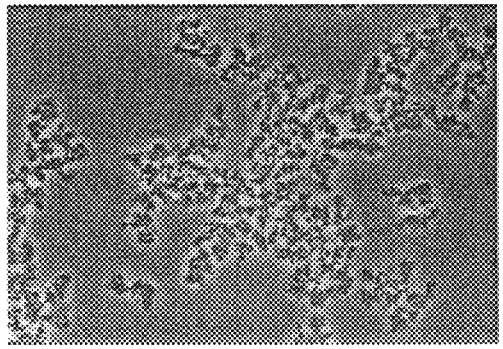
FIG. 2c: Shows a photomicrograph of a composition of 2% Compound A and 1.0% HPC-SL following milling.
Figure 2D:
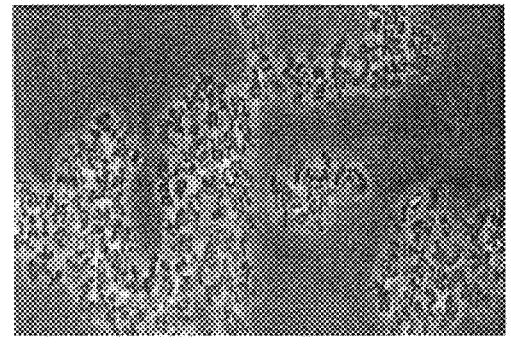
FIG. 2d: Shows a photomicrograph of a composition of 2% Compound A and 1.0% tyloxapol following milling.
Figure 3A:
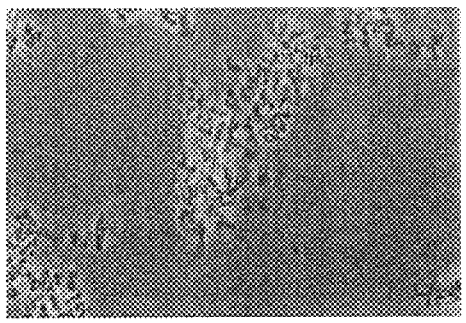
FIG. 3a: Shows a photomicrograph of a composition of 2% Compound A and 1.0% vitamin E PEG following milling.
Figure 3B:
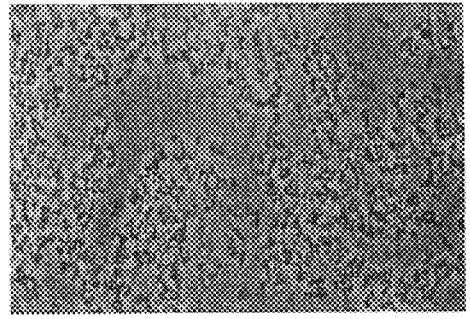
FIG. 3b: Shows a photomicrograph of a composition of 2% Compound A and 1.0% PEG-5000 phospholipid in saline following milling.
Figure 3C:
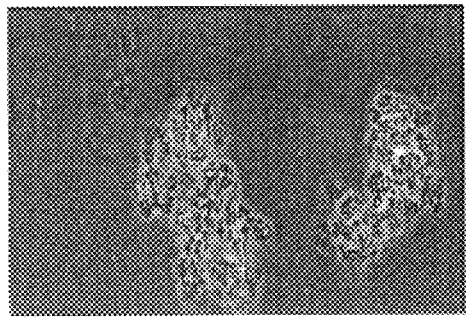
FIG. 3c: Shows a photomicrograph of a composition of 2% Compound A and 1.0% PVP C-15 following milling.
Figure 3D:
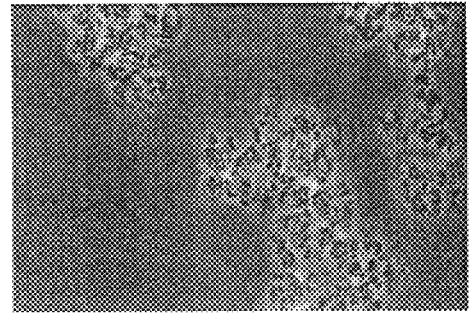
FIG. 3d: Shows a photomicrograph of a composition of 2% Compound A and 2.0% Tween 80 following milling.

(a) a mixture of 2% Compound A and 0.5% albumin (FIG. 1a);

(b) a mixture of 2% Compound A and 1.0% Chremophor EL™ (polyoxyethylated castor oil; BASF Corp.) (FIG. 1b);

(c) a mixture of 2% Compound A and 1.0% Pluronic F108™ (a polyoxyethylene-polyoxypropylene copolymer; BASF Corp.) (FIG. 1c);

(d) a mixture of 2% Compound A and 1.0% Pluronic F108™ in dextrose (FIG. 1d);

(e) a mixture of 2% Compound A, 1.0% Pluronic F108™, and 0.005% DOSS (dioctyl sulfosuccinate; Aldrich Chemicals, Inc.) (FIG. 2a);

(f) a mixture of 2% Compound A and 1.0% Pluronic F108™ in saline (FIG. 2b);

(g) a mixture of 2% Compound A and 1.0% hydroxypropyl cellulose (HPC-SL; Nisso Chemical) (FIG. 2c);

(h) a mixture of 2% Compound A and 1.0% tyloxapol (Nycomed) (FIG. 2d);

(i) a mixture of 2% Compound A and 1.0% vitamin E PEG (vitamin E polyethylene glycol; Eastman Chemical, Rochester, N.Y.) (FIG. 3a);

(j) a mixture of 2% Compound A and 1.0% PEG-5000 phospholipid (Shearwater Polymers, Inc) in saline (FIG. 3b);

(k) a mixture of 2% Compound A and 1.0% Plasdone C-15™ (polyvinylpyrrolidone; GAF Corp.) (FIG. 3c); and (l) a mixture of 2% Compound A and 2.0% Tween 80™ (oleate of a polyoxyethylenated sorbitan; ICI Americas Inc., Wilmington, Del.) (FIG. 3d).

As evidenced by the photomicrographs of the compositions following milling, none of the surfactants resulted in a stable non-agglomerated nanoparticulate composition of Compound A.

EXAMPLE 2

The purpose of this example was to test the effectiveness of a PEG-lipid as an intravenously-acceptable surface stabilizer for nanoparticulate compositions. The active agent tested was Compound A.

Figure 4:
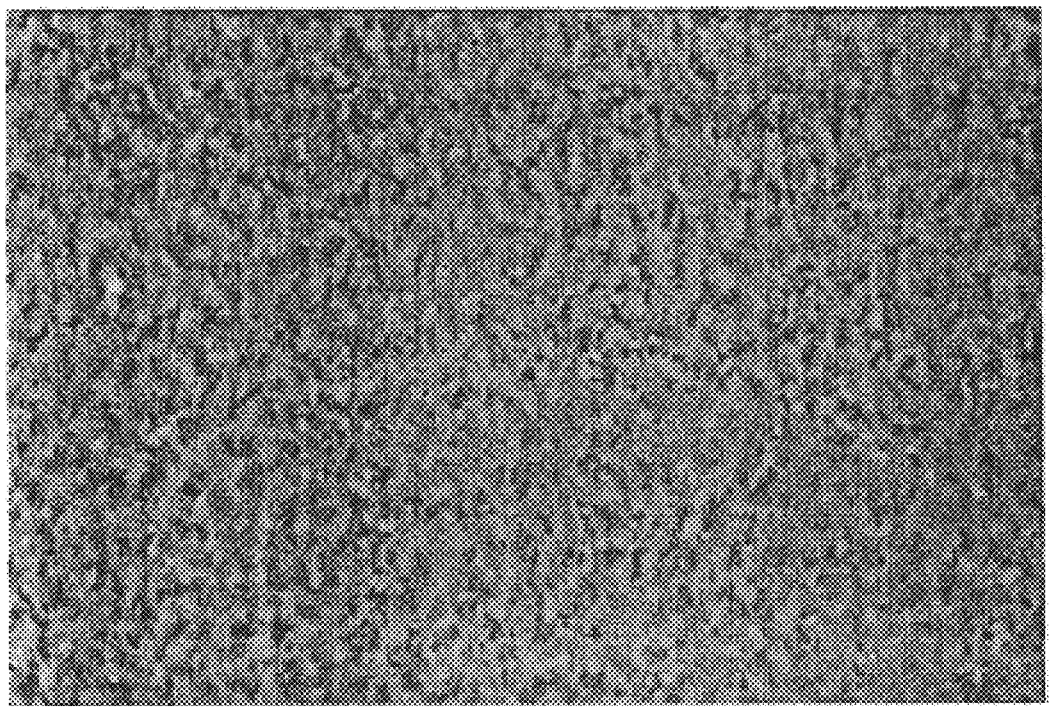
FIG. 4: Shows a photomicrograph of a stable nanoparticulate composition of 2% Compound A and 1.0% PEG-5000 phospholipid following milling.

A mixture of 2% Compound A and 1% PEG-5000™ phospholipid (Shearwater Polymers, Inc.) was roller milled in a 15 ml amber colored bottle filled with 7.5 ml of 0.8 mm YTZ Zirconia media on a U.S. Stoneware mill for 8 days. As shown in FIG. 4, a stable nanoparticulate formulation of Compound A was produced. The final effective average particle size of the nanoparticulate dispersion was about 277 nm, with a standard deviation of about 87 nm. In addition, the resultant nanoparticulate formulation was stable over an extended period of time, i.e., for at least one week at room temperature.

EXAMPLE 3

The purpose of this example was to determine the effectiveness of various intraveneous (IV)-acceptable surface stabilizers, including PEG-lipids, for nanoparticulate compositions. The active agent used was Compound B, a poorly water-soluble pharmaceutically active compound. Compound B, which serves as a dimerizing agent capable of homodimerizing two proteins containing the FKBP domain in a variety of cellular and extracellular contexts, is intended to be used in the treatment of graft versus host disease (GvHD).

Compositions (a), (b), (d), (e), (f), and (g) below were prepared for roller milling in a 15 ml amber colored bottle filled with 7.5 ml of 0.8 mm YTZ Zirconia media on a U.S. Stoneware mill. The compositions were milled for the following time periods: (a)132 hours; (b) 2 weeks; (d) 86 hours; (e) 86 hours; (f) 74 hours; and (g) 127 hours. Compositions (c) and (h )were prepared using the higher energy DC mill in a 15 ml polycarbonate tube filled with 4 ml of 0.5 mm polymeric media. Compositions (c) and (h) were milled for 24 and 20 hours, respectively.

The figures referenced for each composition show a Horiba particle size distribution profile or a micrograph (optical microscopy) of the milled composition.

Figure 5:
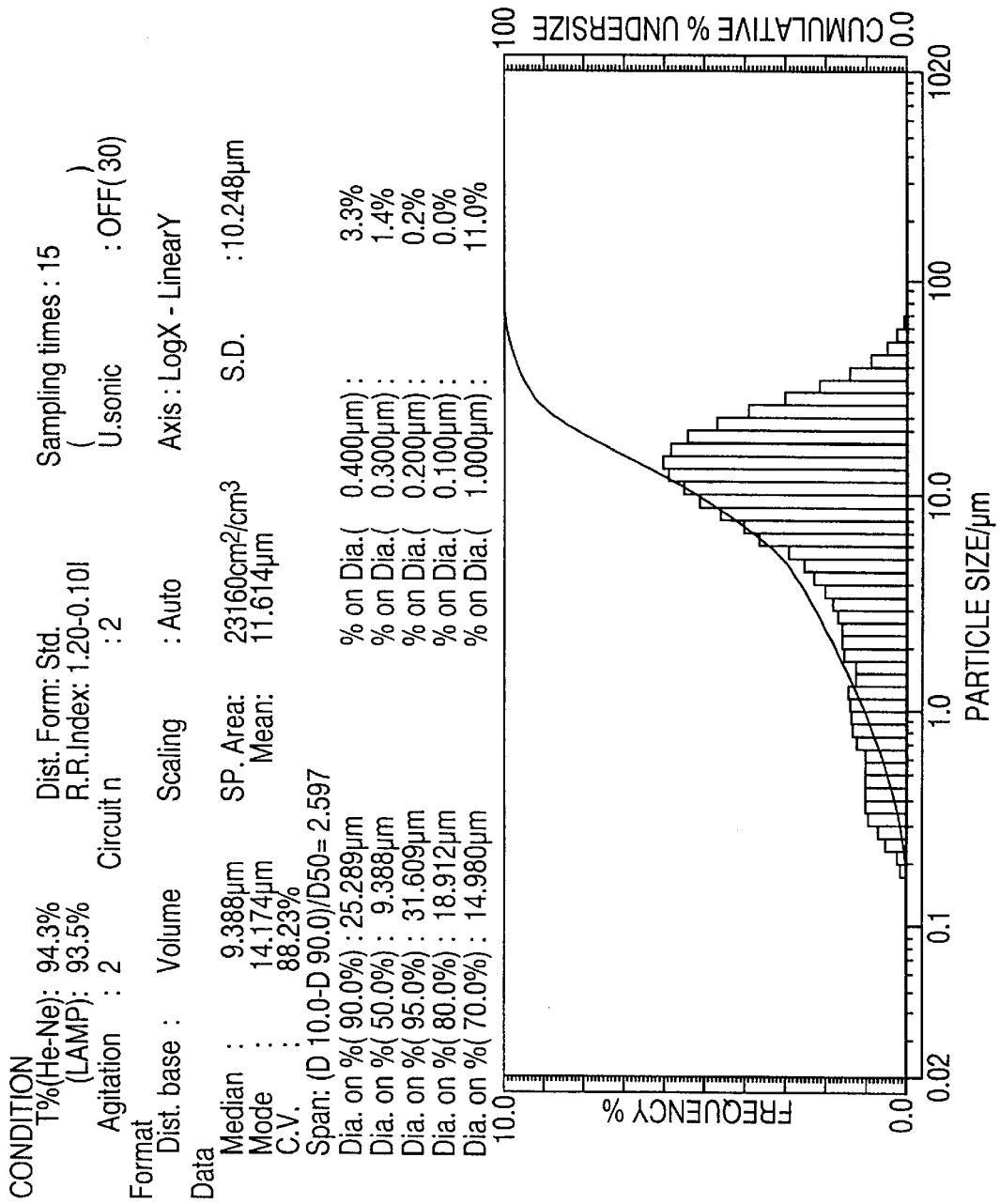
FIG. 5: Shows a Horiba particle size analysis of a milled mixture of 2% Compound B and 2% Pluronic F68™.
Figure 6:
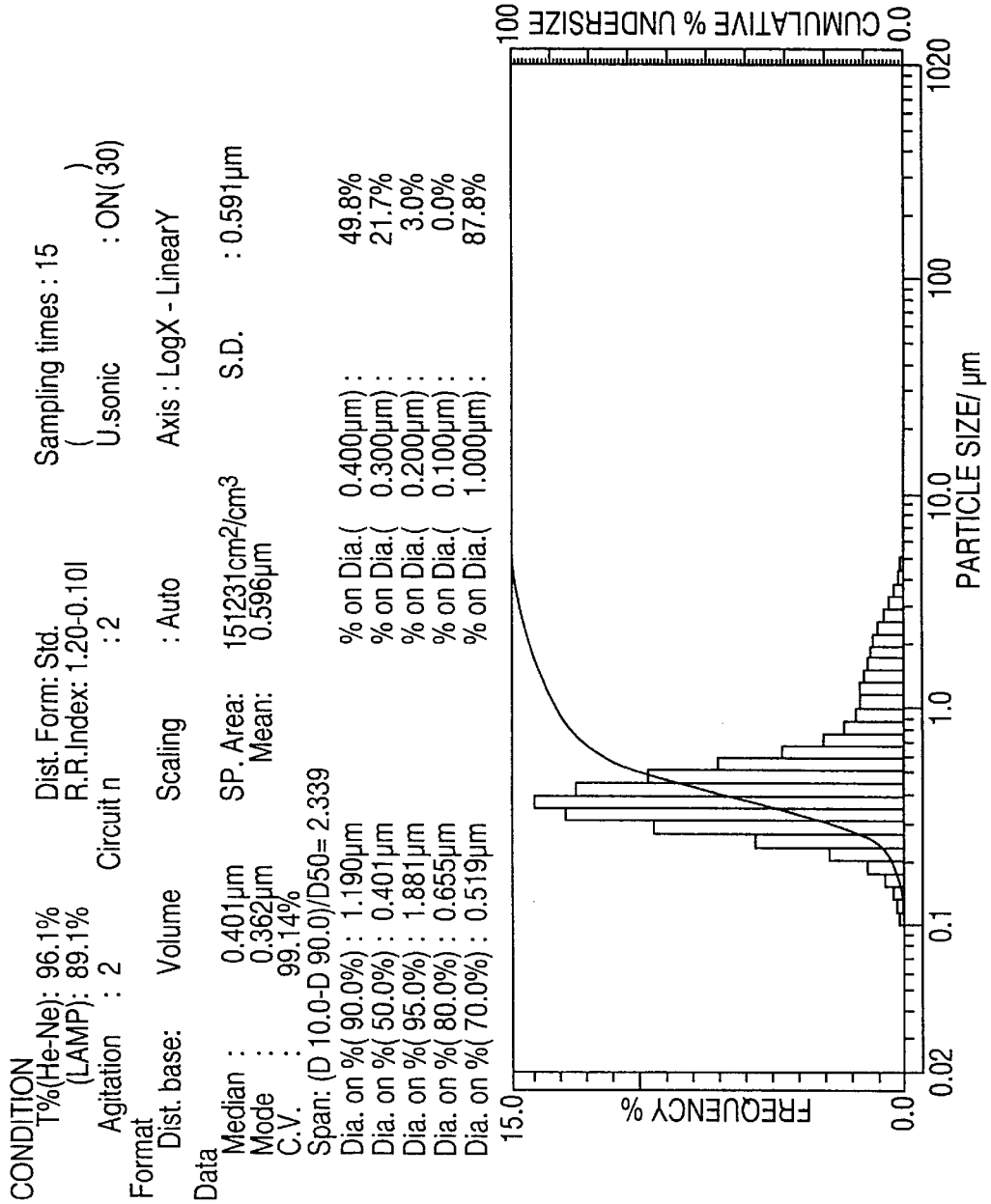
FIG. 6: Shows a Horiba particle size analysis of a milled mixture of 2% Compound B and 2% Plurionic F88™.
Figure 7:
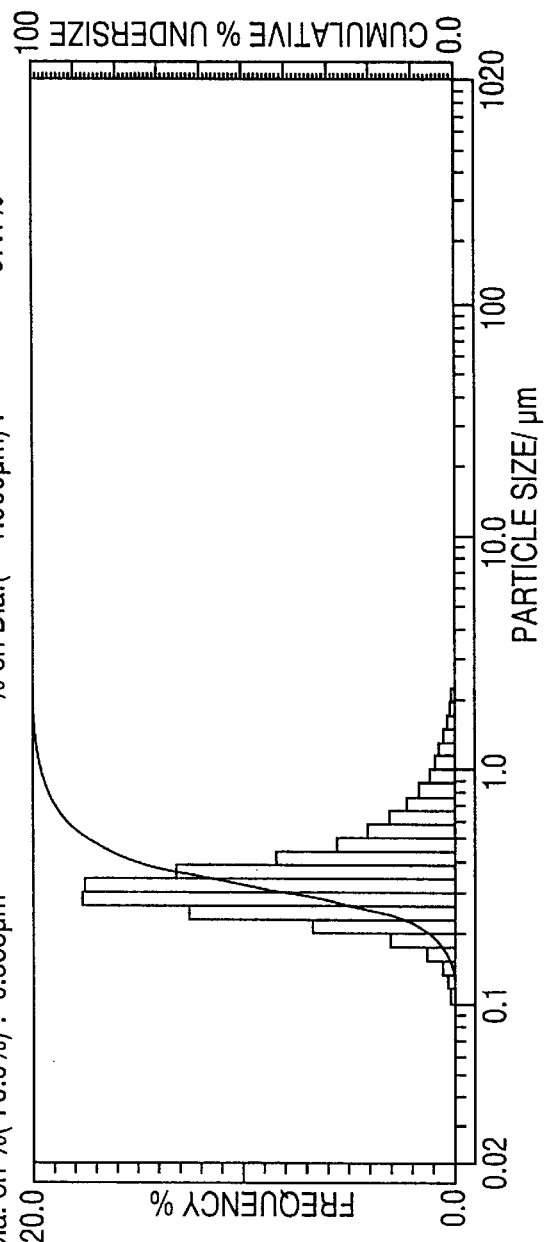
FIG. 7: Shows a Horiba particle size analysis of a milled mixture of 1% Compound B and 1% Plurionic F108™.
Figure 8:
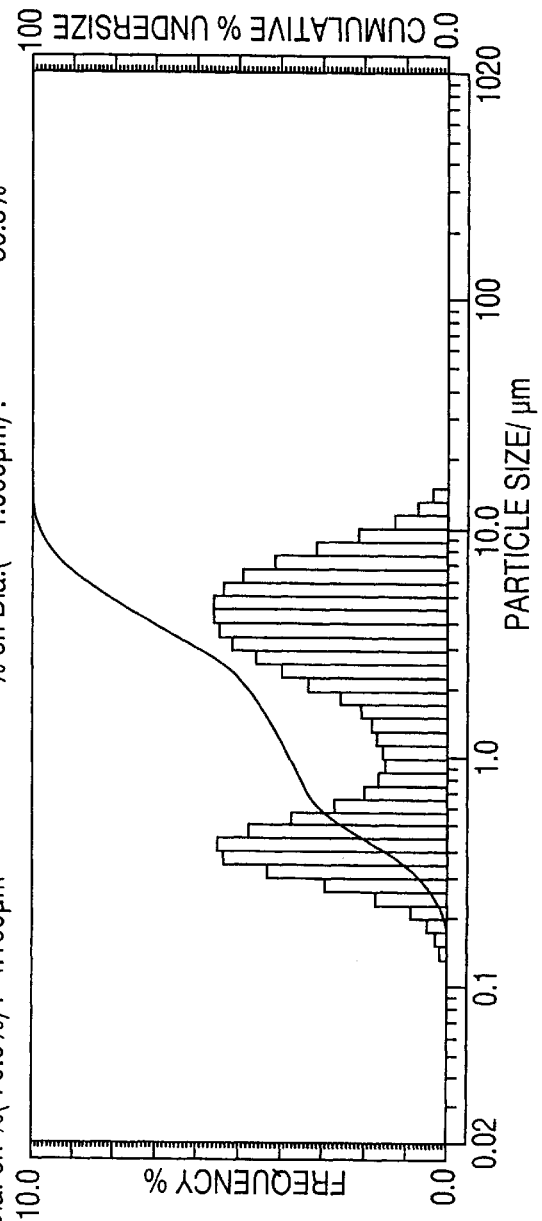
FIG. 8: Shows a Horiba particle size analysis of a milled mixture of 1% Compound B and 0.25% Chremophor EL™.
Figure 9:
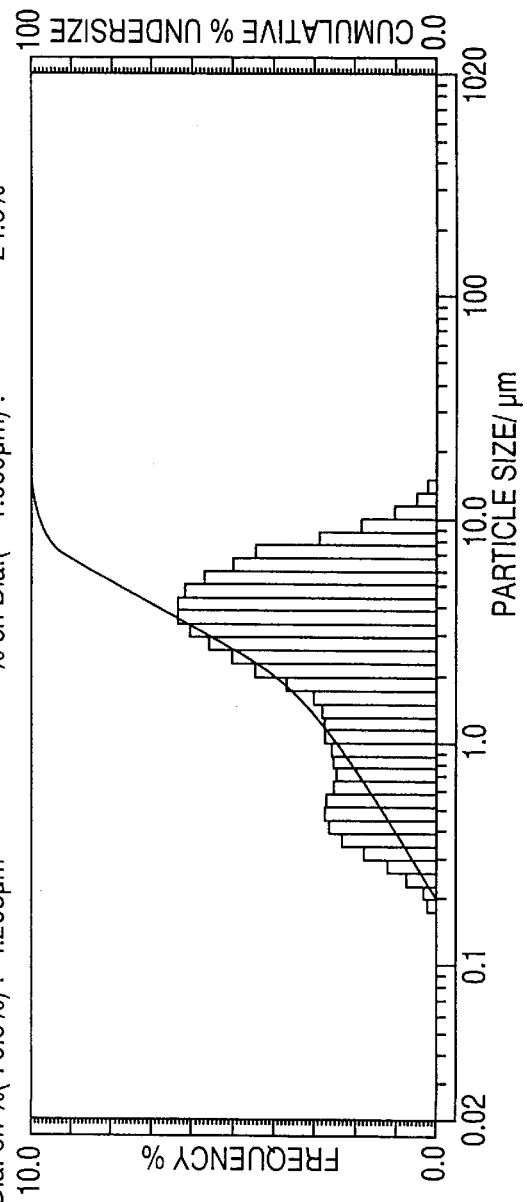
FIG. 9: Shows a Horiba particle size analysis of a milled mixture of 1% Compound B and 0.25% Tween 80™.
Figure 10:
FIG. 10: Shows a photomicrograph of a composition of 2% Compound B and 2% Tyloxapol following milling.
Figure 11:
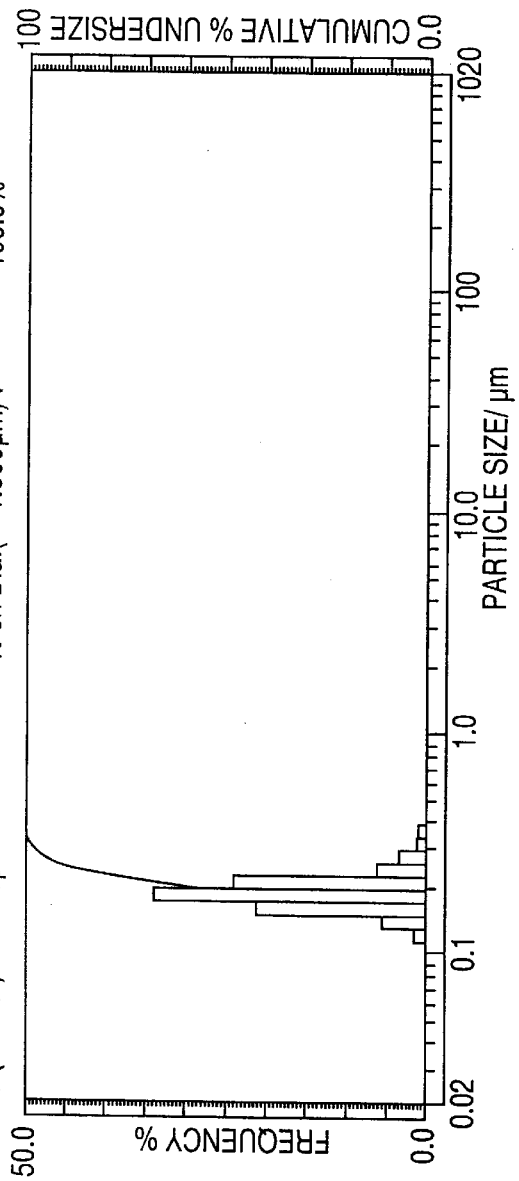
FIG. 11: Shows a Horiba particle size analysis of a milled mixture of 2% Compound B and 1% PEG-5000 Phospholipid.

(a) a mixture of 2% Compound B and 2% Plurionic F68™ (a polyoxyethylene propylene glycol monofatty acid ester; BASF Corp.) (FIG. 5);

(b) a mixture of 2% Compound B and 2% Plurionic F88™ (a polyoxyethylene-polyoxypropylene copolymer; BASF Corp.) (FIG. 6);
(c) a mixture of 1% Compound B and 1% Plurionic F108™ (BASF Corp.) (FIG. 7);
(d) a mixture of 1% Compound B and 0.25% Chremophor EL™ (FIG. 8);
(e) a mixture of 1% Compound B and 0.25% Tween 80™ (FIG. 9);
(f) a mixture of 2% Compound B and 1% PVP C-15; this composition solubilized and, therefore, a colloidal suspension was not formed;
(g) a mixture of 2% Compound B and 2% tyloxapol; this composition formed large particles (FIG. 10); and
(h) a mixture of 2% AP1903 and 1% PEG-5000 Phospholipid (FIG. 11).

FIGS. 5–10 show that the use of Plurionic F68™, Plurionic F88™, Plurionic F108™, Cremophor EL™, Tween 80™, and tyloxapol, produced heterogeneous dispersions, with particle sizes ranging from 1 micron (1000 nm) to 10 microns. Moreover, the minimum particle size obtained was between 300 to 350 mn. In addition, an aggressive milling period was required to obtain small particle sizes with these surface stabilizers.

In contrast, the use of a PEG-lipid surface stabilizer enabled a shorter milling period and produced a well-dispersed colloidal suspension having a maximum particle size of less than about 195 nm. See e.g., FIG. 11.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A nanoparticulate composition comprising an organic drug having at least one polyethylene glycol-derivatized lipid (PEG-lipid) adsorbed on the surface thereof in an amount sufficient to maintain an effective average particle size of less than about 1000 nm, wherein the PEG-lipid is selected from the group consisting of a PEG-phospholipid, PEG-cholesterol, PEG-cholesterol derivative, PEG-vitamin A, and PEG-vitamin E.

2. The composition of claim 1, wherein the drug is present in an amount of about 99.9 to about 10% (w/w).

3. The composition of claim 1, wherein the at least one PEG-lipid is present in an amount of about 0.1 to about 90% (w/w).

4. The composition of claim 1, wherein the drug is selected from the group consisting of a crystalline phase drug and an amorphous phase drug.

5. The composition of claim 1, further comprising at least one surface stabilizer which is not a PEG-phospholipid, PEG-cholesterol, PEG-cholesterol derivative, PEG-vitamin A, or PEG-vitamin E.

6. The composition of claim 1, comprising two or more PEG-lipids selected from the group consisting of PEG-phospholipid, PEG-cholesterol, PEG-cholesterol derivative, PEG-vitamin A, and PEG-vitamin E.

7. An injectable formulation comprising the composition of claim 1.

8. The composition of claim 1, wherein the effective average particle size of the nanoparticulate composition is less than about 600 nm.

9. The composition of claim 1, wherein the effective average particle size of the nanoparticulate composition is less than about 400 nm.

10. The composition of claim 1, wherein the effective average particle size of the nanoparticulate composition is less than about 300 nm.

11. The composition of claim 1, wherein the effective average particle size of the nanoparticulate composition is less than about 200 nm.

12. The composition of claim 1, wherein the effective average particle size of the nanoparticulate composition is less than about 100 nm.

13. The composition of claim 1, wherein the effective average particle size of the nanoparticulate composition is less than about 50 nm.

14. A method of making a nanoparticulate composition, wherein the nanoparticulate composition comprises an organic drug having at least one polyethylene glycol-derivatized lipid (PEG-lipid) adsorbed on the surface thereof in an amount sufficient to maintain an effective average particle size of less than about 1000 nm, said method comprising:
   (a) dispersing particles of the drug in a liquid dispersion medium, and
   (b) applying mechanical means in the presence of grinding media to reduce the particle size of the drug in the liquid dispersion medium to less than about 1000 nm,
wherein: (1) at least one PEG-lipid is added to the liquid dispersion medium before or after milling; and (2) the PEG-lipid is selected from the group consisting of a PEG-phospholipid, PEG-cholesterol, PEG-cholesterol derivative, PEG-vitamin A, and PEG-vitamin E,
   wherein said method produces a nanoparticulate composition having at least one PEG-lipid as a surface stabilizer and an effective average particle size of less than about 1000 nm.

15. The method of claim 14, wherein the drug is present in an amount of about 99.9 to about 10% (w/w).

16. The method of claim 14, wherein the at least one PEG-lipid is present in an amount of about 0.1 to about 90% (w/w).

17. The method of claim 14, wherein the drug is selected from the group consisting of a crystalline phase drug and an amorphous phase drug.

18. The method of claim 14, further comprising at least one surface stabilizer which is not a PEG-phospholipid, PEG-cholesterol, PEG-cholesterol derivative, PEG-vitamin A, or PEG-vitamin E.

19. The method of claim 14, comprising two or more PEG-lipids selected from the group consisting of PEG-phospholipid, PEG-cholesterol, PEG-cholesterol derivative, PEG-vitamin A, and PEG-vitamin E.

20. The method of claim 14, wherein the effective average particle size of the nanoparticulate composition is less than about 600 nm.

21. A method of treating a patient in need with a nanoparticulate composition comprising an organic drug, wherein said method comprises:
   (a) administering to a mammal in need a therapeutically effective amount of nanoparticulate composition having an effective average particle size of less than about 1000 nm and comprising:
      (1) an organic drug;
      (2) at least one polyethylene glycol-derivatized lipid (PEG-lipid) adsorbed on the surface of the drug, wherein the PEG-lipid is selected from the group consisting of a PEG-phospholipid, PEG-cholesterol, PEG-cholesterol derivative, PEG-vitamin A, and PEG-vitamin E.

22. The method of claim 21, wherein the effective average particle size of the nanoparticulate composition is less than about 600 nm.

23. A method of making a nanoparticulate composition, wherein the nanoparticulate composition comprises an organic drug having at least one polyethylene glycol-derivatized lipid (PEG-lipid) adsorbed on the surface thereof in an amount sufficient to maintain an effective average particle size of less than about 1000 nm, said method comprising:

(a) dissolving the drug in a solvent;

(b) adding the solubilized drug to a solution comprising at least one PEG-lipid to form a clear solution;

(c) precipitating the solubilized drug having a PEG-lipid as a surface stabilizer using a non-solvent, wherein the PEG-lipid is selected from the group consisting of a PEG-phospholipid, PEG-cholesterol, PEG-cholesterol derivative, PEG-vitamin A, and PEG-vitamin E, wherein said method produces a nanoparticulate composition having at least one PEG-lipid as a surface stabilizer and an effective average particle size of less than about 1000 nm.

24. The method of claim 23, wherein the drug is present in an amount of about 99.9 to about 10% (w/w).

25. The method of claim 23, wherein the at least one PEG-lipid is present in an amount of about 0.1 to about 90% (w/w).

26. The method of claim 23, wherein the drug is selected from the group consisting of a crystalline phase drug and an amorphous phase drug.

27. The method of claim 23, further comprising at least one surface stabilizer which is not a PEG-phospholipid, PEG-cholesterol, PEG-cholesterol derivative, PEG-vitamin A, or PEG-vitamin E.

28. The method of claim 23, comprising two or more PEG-lipids selected from the group consisting of PEG-phospholipid, PEG-cholesterol, PEG-cholesterol derivative, PEG-vitamin A, and PEG-vitamin E.

29. The method of claim 23, wherein the effective average particle size of the nanoparticulate composition is less than about 600 nm.

30. The method of claim 23, wherein the effective average particle size of the nanoparticulate composition less than about 400 nm.

31. The method of claim 23, wherein the effective average particle size of the nanoparticulate composition less than about 300 nm.

32. The method of claim 23, wherein the effective average particle size of the nanoparticulate composition less than about 200 nm.

33. The method of claim 23, wherein the effective average particle size of the nanoparticulate composition less than about 100 nm.

34. The method of claim 23, wherein the effective average particle size of the nanoparticulate composition less than about 50 nm.

35. The method of claim 21, wherein the drug is present in an amount of about 99.9 to about 10% (w/w).

36. The method of claim 21, wherein the at least one PEG-lipid is present in an amount of about 0.1 to about 90% (w/w).

37. The method of claim 21, wherein the drug is selected from the group consisting of a crystalline phase drug and an amorphous phase drug.

38. The method of claim 21, further comprising at least one surface stabilizer which is not a PEG-phospholipid, PEG-cholesterol, PEG-cholesterol derivative, PEG-vitamin A, or PEG-vitamin E.

39. The method of claim 21, comprising two or more PEG-lipids selected from the group consisting of PEG-phospholipid, PEG-cholesterol, PEG-cholesterol derivative, PEG-vitamin A, and PEG-vitamin E.

40. The method of claim 21, wherein the effective average particle size of the nanoparticulate composition less than about 400 nm.

41. The method of claim 21, wherein the effective average particle size of the nanoparticulate composition less than about 300 nm.

42. The method of claim 21, wherein the effective average particle size of the nanoparticulate composition less than about 200 nm.

43. The method of claim 21, wherein the effective average particle size of the nanoparticulate composition less than about 100 nm.

44. The method of claim 21, wherein the effective average particle size of the nanoparticulate composition less than about 50 nm.

45. The method of claim 14, wherein the effective average particle size of the nanoparticulate composition less than about 400 nm.

46. The method of claim 14, wherein the effective average particle size of the nanoparticulate composition less than about 300 nm.

47. The method of claim 14, wherein the effective average particle size of the nanoparticulate composition less than about 200 nm.

48. The method of claim 14, wherein the effective average particle size of the nanoparticulate composition less than about 100 nm.

49. The method of claim 14, wherein the effective average particle size of the nanoparticulate composition less than about 50 nm.

* * * * *